United States Patent [19]

Stief et al.

[11] Patent Number: 5,464,615

[45] Date of Patent: Nov. 7, 1995

[54] USE OF TRANSGLUTAMINASES AS IMMUNOSUPPRESSANTS

[75] Inventors: Thomas Stief, Sevilla, Spain; Norbert Heimburger; Hans U. Schorlemmer, both of Marburg, Germany

[73] Assignee: Behringwerke Aktiengesellschaft, Marburg, Germany

[21] Appl. No.: 310,038

[22] Filed: Sep. 22, 1994

Related U.S. Application Data

[63] Continuation of Ser. No. 131,879, Oct. 5, 1993, abandoned, which is a continuation of Ser. No. 845,829, Mar. 6, 1992, abandoned, which is a continuation of Ser. No. 399,960, Aug. 29, 1989, abandoned.

[30] Foreign Application Priority Data

Aug. 31, 1988 [DE] Germany ............... 38 29 524.5

[51] Int. Cl.[6] ............... A61K 38/48; A61K 38/55
[52] U.S. Cl. ............... 424/94.63; 424/94.64; 514/2; 514/21; 514/885; 530/381; 530/384
[58] Field of Search ............... 424/94.63, 94.64; 514/2, 21, 885; 530/381, 384

[56] References Cited

U.S. PATENT DOCUMENTS 4,327,086  4/1982  Fukushima et al. ............... 514/21
4,414,976  11/1983  Schwarz et al. ............... 424/530

FOREIGN PATENT DOCUMENTS 0086627  8/1983  European Pat. Off. ..
0278696  8/1988  European Pat. Off. ..
0278416  8/1988  European Pat. Off. ..

OTHER PUBLICATIONS

G. Dickneite, et al "The Immunosuppressive Properties of 15–Deoxysperqualin and Its Effects on Experimental Skin and Islet Cell Transplantation," Recent Advances in Chemotherapy, Anticancer Section 2, Proceedings of the 14th International Congress of Chemotherapy, Kyoto, pp. 949–950 1985.

Suzuki et al, Thronbosis and Haemostasis, vol. 58(1) Jul. 1987, abstract 509.

"Report of the Meeting of the Subcommittee on Fibrinolysis, Gerusalem, Israel, Jun. 2, 1986", Thromb. Tfaem., 56, 415–416.

Primary Examiner—Jacqueline M. Stone
Assistant Examiner—John LeGuyader
Attorney, Agent, or Firm—Finnegan, Henderson, Farabow, Garrett & Dunner

[57] ABSTRACT

A description is given of the possibility of using transglutaminases in a process for the preparation of an immunosuppressant.

Additionally described is a pharmaceutical containing a transglutaminase and a plasminogen activator inhibitor.

4 Claims, No Drawings

USE OF TRANSGLUTAMINASES AS IMMUNOSUPPRESSANTS

This application is a continuation of application Ser. No. 08/131,879, filed Oct. 5,1993, now abandoned, which is a continuation of application Ser. No. 07/845,829, filed Mar. 6, 1992, abandoned, which is a continuation of application Ser. No. 07/399,960, filed Aug. 29, 1989, abandoned.

The invention relates to the use of a transglutaminase in a process for the preparation of an immunosuppressant.

Macrophage and polymorphonuclear neutrophilic leukocytes (PMN) are essentially involved in the immune response of the body. They have an attack system which comprises proteases on the one hand and potent oxidizing agents (N-chloroamines and oxygen radicals) on the other. They influence and enhance the immune response via these proteases and oxidizing agents.

By immune response is meant the reaction of immunocompetent cells such as the monocyte/macrophage system to stimulators of inflammation, infection, tissue transformation and tissue repair. The monocyte/macrophage system performs a wide variety of tasks throughout the body because monocytes migrate from the blood into a wide variety of tissues where they undertake, not least, specific immunological tasks. Thus, the monocytes differentiate into alveolar macrophages in the lung, into Kupffer's cells in the liver, into osteoclasts in bone, into microglial cells in the central nervous system (CNS), into mesangial macrophages in the kidney, into surface cells in the synovial membrane, and into pleural or peritoneal macrophages in the body cavities.

Inhibitors of these macrophages and PMN are of great clinical interest because a large number of human diseases is associated with increased macrophage activity.

There may be circumstances in which suppression of the function of one or more compartments of the immune system is desirable. Possible circumstances of this nature are a reaction of the immune system which goes beyond the normal extent (hyperergic state) or a reaction of the immune system against the body's own tissue.

Substances which are able to inhibit the biological action of macrophages can act as immunosuppressants. There is a great need for immunosuppressants which a) have few side effects and b) are highly specific. The corticoid derivatives which are widely used clinically comply with neither a) nor b).

When substances which act to inhibit the secretion of oxygen radicals were tested in in vitro test systems with macrophages it was found, surprisingly, that inhibitors of ornithyl decarboxylase, especially of the transglutaminase type, preferably F XIII, originating both from the placenta and from the plasma, have, in physiological concentrations, potent inhibiting effects on the chemiluminescence reaction, which derives from the release of oxygen radicals, of macrophages.

It has additionally been found, surprisingly, that F XIII has an immunosuppressant action in vivo in models of transplantation.

The invention therefore relates to the use of a transglutaminase, preferably of factor XIII, for the preparation of an immunosuppressant.

Examples of pathological states in which an immunosuppressant of this type can be used are those with a chronic inflammatory process such as rheumatoid arthritis, Crohn's disease, ulcerative colitis, multiple sclerosis, Guillain-Barré syndrome, psoriasis and other autoimmune diseases, degenerative disorders such as Parkinson's disease, arteriosclerosis, neoplastic diseases, hyperergic/allergic disorders, graft-versus-host reactions, shock syndrome such as ARDS (adult respiratory distress syndrome), post-burn disorder, consumption Coagulopathy and sepsis. An agent of this type may also be important for infectious diseases such as AIDS.

The transplantation of exogenous tissue is also followed by an immunological reaction against the transplanted organ which is recognized as foreign or against the recipient organism in the nature of a graft-versus-host reaction, which leads to rejection. Rejection crises of this nature may also arise with placental tissue which in some cases is also recognized by the mother's body as foreign and may lead to placenta/trophoblast disturbances and premature detachment of the placenta. It is therefore necessary to suppress the immune system of the organ recipient or of the transplant in order to ensure the survival of the transplant or of the recipient.

In contrast to superoxide dismutase which is used clinically and which is able to neutralize superoxide ions which have been produced, F XIII prevents the production of superoxide ions. Transglutaminases also act on allergic encephalomyelitis (AE) which is regarded as a disease model of the human disease multiple sclerosis.

There may also be a contribution to the causation of neoplastic diseases by a pathologically increased activity of leukocytes. These include, for example, histocytosis X, leukemias, preferentially of the myeloid series and certain tumors which behave like macrophages or tumors which depend on assistance from macrophages (for example to supply the tumor stroma in the sense of anglogenesis). Hence the immunosuppressive therapy according to the invention is likewise advisable for these neoplastic diseases.

Reactions of the immune system going beyond the normal, and pathologically elevated release of oxygen radicals and/or plasminogen activators associated therewith, also occur in reperfusion states, i.e. a sudden flow of blood through a previously hypoperfused tissue, when breathing a high percentage of oxygen, on clinical use or poisoning with, for example, paraquat, treatment with cisplatin, adriamycin, nitrofurantoin, bleomycin, streptozotocin and other diabetogenic substances, irradiation therapy and tissue damage associated therewith.

Measures known to be suitable for suppressing the immune system include treatment with antibodies against lymphatic tissue, with ionizing radiation and with chemical substances. An aggressive treatment of this nature is associated with pronounced side effects: organotoxicity, sterility with cytostatics and ionizing radiation, cerebral edema with tranexamic acid, anti-antibody formation with the risk of a serum disease on treatment with antibodies.

By contrast a use of human physiological F XIII has none of the side effects and acts considerably more effectively even at low doses. It appears that no adverse effects are induced even by high concentrations of F XIII in human plasma, so that the therapeutic index of this protein is evidently high (at least up to 10 times the normal plasma concentration). An effective amount of transglutaminases for inhibiting the damage in tissue at risk during reperfusion, in inflammatory processes, subarachnoid hemorrhages, autoimmune diseases, degenerative disorders, arteriosclerosis, neoplastic diseases (such as leukemias, histiocytosis X and others), hyperergic/allergic disorders, post-burn disorder, transplant incompatibility, premature detachment of the placenta and pre-eclampsia, shock syndrome, depends on a number of factors, for example the age and the weight of the patient and the clinical condition.

An effective dose of a transglutaminase are preferably F XIII, is about 0.7–3000, particularly preferably 7– 300

U*/kg/24 hours, which can be administered i.v. or, solubilized, i.mm. Transglutaminases such as F XIII can be stabilized by addition of stabilizers such as albumin, polygeline or an amino acid such as glycine (* 1 U corresponds to the amount of F XIII in 1 ml of human citrated plasma ).

Transglutaminases such as F XIII can also be administered topically for the local therapy and prophylaxis of disturbances of wound healing, transplant rejections, asthmoid bronchial disorders, burns and other disorders associated with increased macrophage activity.

There are medical indications for combinations of transglutaminases and a fibrinolytic such as tissue plasminogen activator (tPA), urokinase, streptokinase, or plasminogen streptokinase activator complex for lysis therapy preferably of arterial occlusions such as in myocardial infarct or stroke. Combined use of transglutaminases and fibrinolytics makes it possible immediately to inhibit tissue damage such as, for example, necroses during and after acute reperfusion owing to hyperactive white blood cells.

Additionally indicated are combinations of transglutaminases with antithrombin III derived from human plasma or by genetic manipulation for use as an immunosuppressant.

Medically indicated in a preferred manner are combinations of transglutaminases with plasminogen activator inhibitor of placental origin (PAI-2) for use as an immunosuppressant. When PAI-2 is used in combination with transglutaminases the effective dose of PAI-2 is, in general, 7–3,000 urokinase-inhibiting units/kg/24 hours, i.e. 525–225,000 units for a patient weighing 75 kg for systemic administration.

The effect of transglutaminases on the immune response of mice and of humans is illustrated by way of example hereinafter in selected standard in vivo and in vitro test methods which are known to be used for assessing immunosuppressors. The experiments were carried out with purified placental F XIII. A check with purified plasma F XIII gave comparable results.

Example 1

Effect of factor XIII on the stimulation of human phagocytes in vitro—additive effect of F XIII plus plasminogen activator inhibitor-2

Polymorphonuclear granulocytes and mononuclear phagocytes were obtained from the peripheral blood of healthy donors and tested for various functions after administration of the product. The parameters of phagocyte function investigated were the chemiluminescence reaction and the secretion of lysosomal enzymes. The effect of factor XIII both on non-activated phagocytes (−IC) and on phagocytes activated by immune complexes (+IC) was measured.

Compared with phagocytes from the corresponding control groups (untreated cells) the chemiluminescence reaction (generation of oxygen radicals) was significantly and dose-dependently reduced with both human granulocytes and monocytes (phagocytes) (Table 1 ).

This suppressant action of factor XIII is even more pronounced on costimulation in vitro with immune complexes IC (50 µg/ml). Human mononuclear phagocytes which are treated with the substance are also particularly distinguished by the secretion of lysosomal enzymes thereof being distinctly inhibited (Table 2). When 0.05 U of F XIII is given in combination with 0.1 U of placental plasminogen activator inhibitor (PAI)-2 under IC stimulation the resulting inhibition is to below 40%, despite an inhibition of about 50% by the individual substances, which reveals an additive/synergistic mode of action of the two substances.

Example 2

Effect of factor XIII on the activity of mouse peritoneal macrophages in vivo

Factor XIII was administered parenterally in concentrations of 0.25–2.5 U/animal to female NMRI mice (18–20 g). The controls received the same volumes (0.5 ml) of the solvent (physiologically buffered saline solution, pH 7.2). Two hours and 24 hours later the mice were sacrificed, the macrophages were removed from their abdominal cavities, and the determination of the activity was carried out by means of chemiluminescence as described in Example 1. As is evident from Table 3, factor XIII reduces the activity of macrophages taken from mice previously treated with the product. The suppression was observed in the chemiluminescence both 2 hours and 24 hours after administration of the substance with and without addition of immune complexes in vitro.

Example 3

Effect of F XIII on the survival time of transplanted skin from the rat tail

In this design of experiment, pieces, about 0.5×1.0 cm in size, of tail skin from Lewis rats were transplanted onto the tail of Fischer rats. The transplanted pieces of skin are recognized as foreign by the immune system of the recipient animals and are rejected. As is evident from Table 4, the survival time of transplants in the Lewis/Fischer rat model was between 16 and 18 days in the control groups which were treated only with the solvent. Factor XIII (5 U/animal) was administered intraperitoneally on 7 consecutive days starting either on day 1 or on day 10 after transplantation. It emerged from this, surprisingly, that factor XIII in the concentration used increased the survival times of the transplants from 17.0±4 to 24.8±1.9 and 26.8±2.2.

TABLE 1

Effect of factor XIII on oxidative metabolism (chemiluminescence) with and without stimulation by immune complexes (50 µg/ml) in vitro

| Cell type | Factor XIII (U/ml) | Chemiluminescence Integrated RLU/15 min (×10³) | |
|---|---|---|---|
| | | −IC | +IC |
| Human monocytes (phagocytes) 1 × 10⁶ cells | 0 | 1674 ± 245 | 19775 ± 1450 |
| | 2.5 | 252 ± 48 | 947 ± 152 |
| | 1.2 | 384 ± 95 | 1294 ± 58 |
| | 0.6 | 474 ± 61 | 2195 ± 35 |
| | 0.3 | 575 ± 61 | 5195 ± 488 |
| | 0.03 | 637 ± 81 | 6850 ± 354 |
| | 0.01 | 873 + 75 | 10055 + 629 |
| Human granulocytes 2 × 10⁵ cells | 0 | 2678 ± 353 | 58650 ± 2124 |
| | 2.5 | 148 ± 24 | 6448 ± 1505 |
| | 1.2 | 342 ± 31 | 9583 ± 1193 |
| | 0.6 | 645 ± 68 | 15733 ± 2035 |
| | 0.3 | 863 ± 51 | 18700 ± 1114 |
| | 0.03 | 1075 ± 134 | 26900 ± 1556 |
| | 0.01 | 1226 ± 186 | 37400 ± 2851 |

RLU = relative light units

TABLE 2

Effect of factor XIII on macrophage activity
(human monocytes, 3 × 10⁶ cells) in vitro.

| Factor XIII (units/ml) | Enzyme release (N—Ac—Glu, mU/ml) | |
| --- | --- | --- |
|  | −IC | +IC |
| 0 | 8365 ± 219 | 16205 ± 1703 |
| 2.5 | 2514 ± 574 | 2723 ± 333 |
| 0.6 | 4254 ± 541 | 6428 ± 1112 |
| 0.3 | 6358 ± 632 | 10320 ± 1030 |
| 0.03 | 7703 ± 288 | 13483 ± 794 |

TABLE 3

Effect of factor XIII on macrophage activity
(1 × 10⁶ cells) in vivo.

| Factor XIII U/animal 1 × i.p. | Chemiluminescence Integrated RLU/15 min. (×10³) | | | |
| --- | --- | --- | --- | --- |
|  | −IC | | +IC | |
|  | 2 h | 24 h | 2 h | 24 h |
| 2.5 | 268 ± 54 | 496 ± 79 | — | 4463 ± 567 |
| 1.0 | 512 ± 103 | 959 ± 163 | — | 8485 ± 707 |
| 0.5 | 981 ± 111 | 1290 ± 240 | — | 11300 ± 1424 |
| 0.25 | 1113 ± 67 | 2105 ± 276 | — | 16233 ± 2706 |
| 0 | 2775 ± 375 | 4480 ± 453 | — | 36767 ± 3227 |

TABLE 4

Effect of factor XIII on skin transplantation in Fischer rats

| Substance | Days of transplant rejection | Mean (days) (x ± s) |
| --- | --- | --- |
| Control | 19, 18, 16, 16, 16 | 17.0 ± 1.4 |
| Factor XIII 5 U/animal, 7 × i.p. day 1–7 | 22, 27, 24, 26, 25 | 24.8 ± 1.9 |
| Factor XIII 5 U/animal, 7 × i.p. day 10–17 | 30, 27, 24, 27, 26 | 26.8 ± 2.2 |

We claim:

1. A method of treating a patient in need of suppression of the immune response in transplant rejection by administering to such patient an effective amount of an immunosuppressant agent comprising a transglutaminase with a pharmaceutically acceptable excipient.

2. A method of treating a patient as claimed in claim 1 wherein the transglutaminase is factor XIII.

3. A method of treating a patient as claimed in claim 1 in need of suppression of the monocyte-macrophage system.

4. A method of treating a patient as claimed in claim 1 wherein a composition containing 52.5 to 225,000 units per dose of transglutaminase is administered.

* * * * *